US00PP37477P2

(12) United States Plant Patent
Nannes

(10) Patent No.: US PP37,477 P2
(45) Date of Patent: Jun. 16, 2026

(54) ***PEPEROMIA* PLANT NAMED 'BINL-77430001'**

(50) Latin Name: *Peperomia clusiifolia*
Varietal Denomination: BINL-77430001

(71) Applicant: Botanical Innovation B.V., Wageningen (NL)

(72) Inventor: Jacobus A.M. Nannes, Nairobi (KE)

(73) Assignee: Botanical Innovation B.V. (NL)

( * ) Notice: Subject to any disclaimer, the term of this patent is extended or adjusted under 35 U.S.C. 154(b) by 0 days.

(21) Appl. No.: 19/344,982

(22) Filed: Sep. 30, 2025

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

(56) References Cited

U.S. PATENT DOCUMENTS

PP33,007 P2 * 4/2021 Smit ..... Plt./373

* cited by examiner

*Primary Examiner* — Susan McCormick Ewoldt
*Assistant Examiner* — Zachariah Allan Kay

(57) ABSTRACT

A new and distinct cultivar of *Peperomia* plant named 'BINL-77430001' is disclosed, characterized by distinct variegated leaves with a unique combination of colors. Variegated leaves have an irregular light green and medium green center, fading out into an irregular thick yellow leaf margin. All mature leaves have a very thin pink-red leaf-rim. The new cultivar is a *Peperomia*, typically used as an ornamental plant.

2 Drawing Sheets

Figure 1:
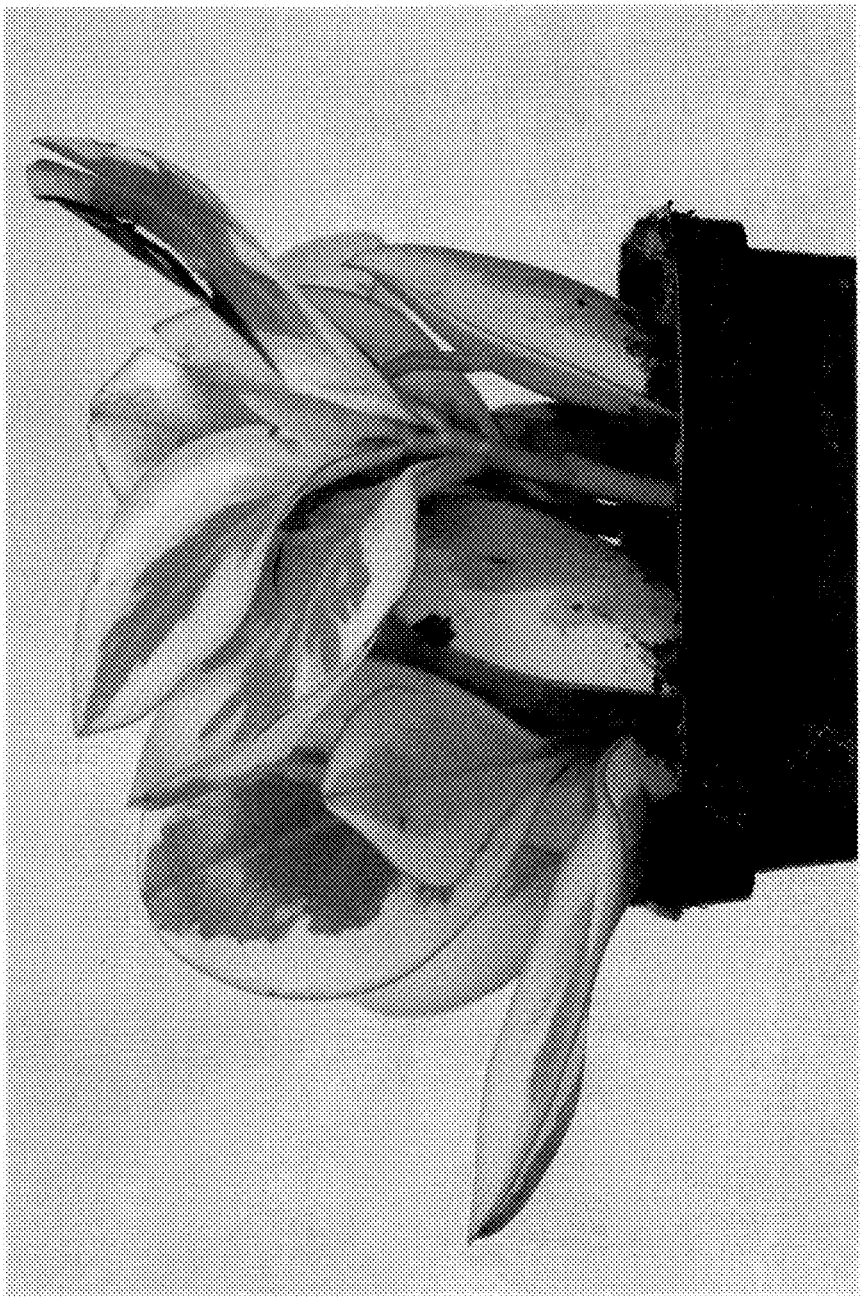

Latin name of the genus and species: *Peperomia clusiifolia.*

Cultivar denomination: 'BINL-77430001'.

BACKGROUND OF THE INVENTION

The new cultivar is a product of a naturally-occurring branch mutation of the cultivar *Peperomia clusiifolia*, 'Red Margin', unpatented. 'BINL-77430001' was found and selected by the inventor in May 2019 at a nursery in Nairobi, Kenya.

Asexual reproduction of the new cultivar 'BINL-77430001' by terminal and stem cuttings was first performed in Nairobi, Kenya in August 2019, and has shown that the unique features of this cultivar are stable and reproduced true to type through successive generations.

SUMMARY OF THE INVENTION

The cultivar 'BINL-77430001' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BINL-77430001'. These characteristics in combination distinguish 'BINL-77430001' as a new and distinct *Peperomia* cultivar:

1. Distinct variegated leaves with a unique combination of colors. Variegated leaves have an irregular light green and medium green center, fading out into a large irregular yellow leaf margin. All mature leaves have a very thin pink-red leaf rim.

PARENT COMPARISON

Plants of the new cultivar 'BINL-77430001' are similar to plants of the parent plant in most horticultural characteristics, however, plants of the new cultivar 'BINL-77430001' differ from in the following characteristics:

1. Leaf color of the new cultivar is variegated with an irregular light green and medium green center, fading out into a large irregular yellow leaf margin. All mature leaves have a very thin pink-red leaf-rim. Leaf color of the parent is non-variegated, having a glossy, solid dark green color and a dark purple leaf-rim.

COMMERCIAL COMPARISONS

Plants of the new cultivar 'BINL-77430001' are similar to plants of the commercial cultivar *Peperomia clusiifolia* 'Ginny', unpatented. However, plants of the new cultivar differ in the following characteristics:

1. Leaf color of the new cultivar is variegated with an irregular light green and medium green center, fading out into a large irregular yellow leaf margin. All mature leaves have a very thin pink-red leaf-rim. Leaf color of this comparator is variegated with a much bigger irregular light green-green center, fading out into a smaller irregular yellow-white leaf outside. All mature leaves also have a pink-red leaf-rim, however it is less defined and more flushed in appearance.
2. Leaves of the new cultivar are approximately 50% shorter than leaves of this comparator.

Plants of the new cultivar 'BINL-77430001' are similar to plants of the commercial cultivar *Peperomia clusiifolia* 'Variegata', unpatented. However, plants of the new cultivar differ in the following characteristics:

1. Leaf color of the new cultivar is is variegated with an irregular light green and medium green center, fading out into a large irregular yellow leaf margin. All mature leaves have a very thin pink-red leaf-rim. Leaf color of this comparator is variegated with an irregular light green-green center, fading out into a creamy white leaf-outside, without a colored leaf-rim.

2. Leaves of the new cultivar are more elongated than leaves of this comparator.

BRIEF DESCRIPTION OF THE PHOTOGRAPHS

The accompanying photograph in FIG. 1 illustrates in full color a typical plant of 'BINL-77430001' grown in a greenhouse. The plant is approximately 8 weeks of age.

Figure 2:
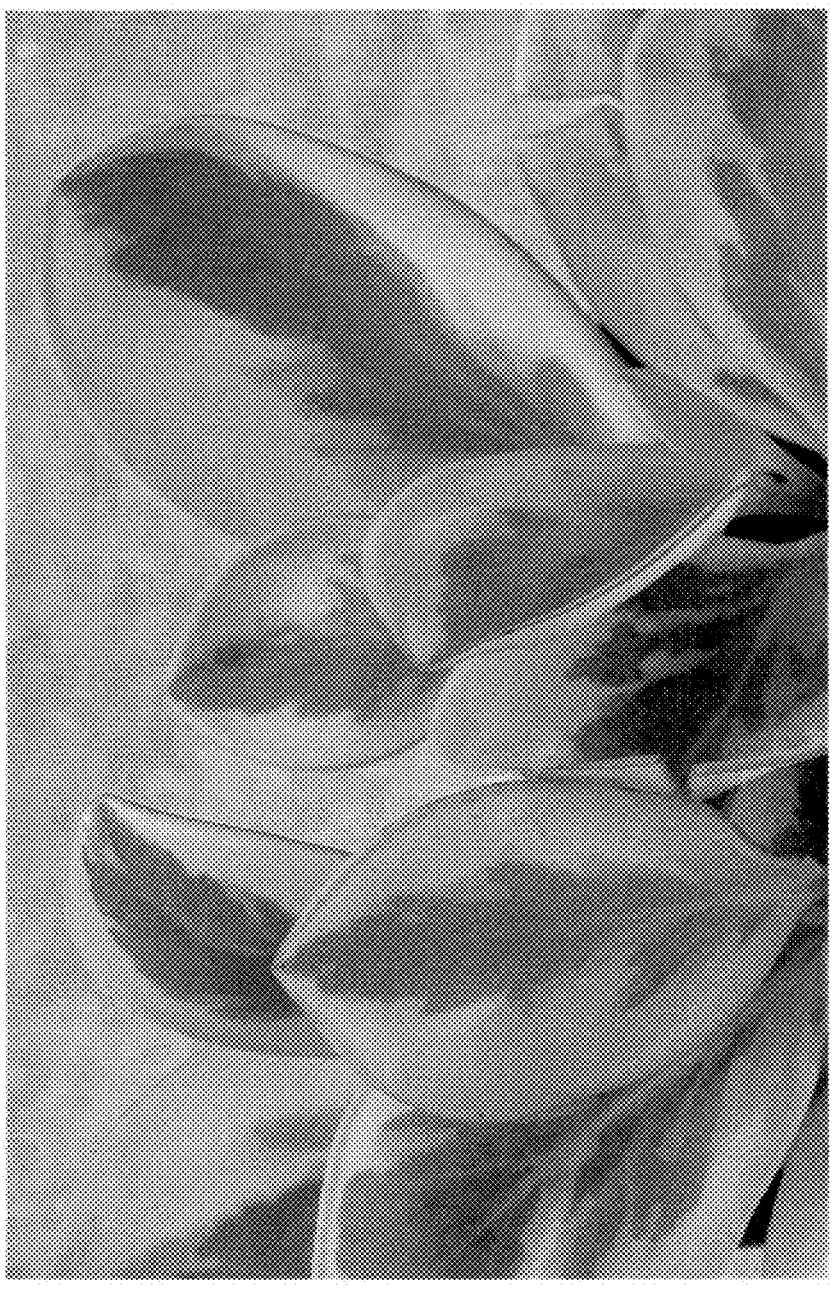

FIG. 2 illustrates a close-up of the foliage.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'BINL-77430001' plants at 8 weeks of age, grown in a greenhouse in August in Nairobi, Kenya. The growing temperature ranged from 18° C. to 20° C. at night to 20° C. to 28° C. during the day. Measurements and numerical values represent averages of typical flowering types.

Botanical classification: *Peperomia clusiifolia* 'BINL-77430001'.

PROPAGATION

Time to initiate roots: About 14 days at 20° C. in summer; 21 days at 20° C. in winter.

Time to produce rooted cutting: About 45 days at 20° C. in summer; 60 days at 20° C. in winter.

Description of roots: Fleshy, medium thickness, moderately dense, moderate branching. White in color, not accurately measured with R.H.S. chart.

PLANT

Plant type: Tender perennial potted plant.

Plant shape: Obovate.

Growth habit: Main stems grow from the base, no lateral branches present.

Plant spread: 7.5 cm.

Height: 9.6 cm.

Growth rate: Moderate.

Plant vigor: Moderate.

Age of plant described: Approximately 8 weeks.

Branching habit: Main stems grow from the base, no lateral branches present.

Pinching: Pinching not required.

Number of primary (main) branches per plant: Average 1.

Main branches:

- Length: Average: 4.7 cm.
- Diameter: Average: 5 mm.

Internode length: Average: 1.4 mm.

Appearance and shape: Circular.

Luster: Glossy.

Aspect/angle from vertical: Average 0° from vertical.

Strength: Moderately strong.

Color:

- *Developing*.—RHS Greyed-Orange 174A and 176A.
- *Mature*.—Near RHS Greyed-Green 197A.
- *At internodes*.—Near RHS Greyed-Green 197A, tinged Yellow-Green 146D.

Pubescence: None.

Plant fragrance: None.

FOLIAGE

Leaf:

- *Arrangement*.—Alternate, single.
- *Quantity*.—Average 4.
- *Average length*.—6.4 cm.
- *Average width*.—3.9 cm.
- *Shape of blade*.—Elliptic to obovate.
- *Whole leaf aspect*.—Concave.
- *Apex*.—Bluntly acute to rounded.
- *Base*.—Attenuate.
- *Margin*.—Slightly revolute.
- *Texture of top surface*.—Glabrous, smooth, moderately leathery.
- *Texture of bottom surface*.—Glabrous, smooth, moderately leathery.
- *Pubescence*.—None.
- *Luster, upper side*.—Moderately glossy.
- *Luster, under side*.—Matte.
- *Rugosity*.—Both sides non-rugose.
- *Color*.—Young foliage upper side: Near RHS Yellow-Green N144B, center 144B, thinly edged Greyed-Purple 184B. Young foliage under side: RHS Yellow-Green N144D, center blotched Green 138B and 138C, thinly edged Greyed-Purple 184B. Mature foliage upper side: Center RHS Green 139A and Greyed-Green 191A, irregularly blotched Greyed-Green 194B, irregularly, broadly margined Yellow-Green 151D and 154D, thinly edged Greyed-Purple 185A. Mature foliage under side: Center Greyed-Green 194C, irregularly, broadly margined Yellow-Green 150D, thinly edged Greyed-Purple 184A.
- *Venation*.—Pattern: Pinnate. Venation color upper side: Main vein RHS Greyed-Green 194C. Venation color under side: Main vein RHS Yellow-Green 144A, 147A towards the top.
- *Petiole*.—Average Length: 0.3 cm. Diameter: Petiole u-shaped, average horizontal and vertical diameter 0.3 cm. Texture: Glabrous, smooth, moderately leathery. Luster: Both sides matte. Strength: Moderately strong. Color, upper side: RHS Greyed-Red 181B, 183C towards the base. Color, under side: RHS Greyed-Red 178B.

FLOWER

Flowers not observed to date.

REPRODUCTIVE ORGANS

Not observed.

OTHER CHARACTERISTICS

Seeds and fruits: None observed to date.

Disease/pest resistance: Neither resistance nor susceptibility to normal diseases and pests of *Peperomia* observed.

Temperature and environmental tolerance: Tolerates temperatures from 5° C. to 35° C. Intolerant to wind and rain.

What is claimed is:

1. A new and distinct cultivar of *Peperomia* plant named 'BINL-77430001' as herein illustrated and described.

* * * * *